United States Patent [19]

Popil

[11] Patent Number: 5,162,660
[45] Date of Patent: Nov. 10, 1992

[54] PAPER ROUGHNESS OR GLASS SENSOR USING POLARIZED LIGHT REFLECTION

[75] Inventor: Roman E. Popil, White Rock, Canada

[73] Assignee: MacMillan Bloedel Limited, Vancouver, Canada

[21] Appl. No.: 722,435

[22] Filed: Jun. 27, 1991

[51] Int. Cl.$^5$ ............................................. G01N 21/86
[52] U.S. Cl. ..................................... 250/561; 250/225
[58] Field of Search ............... 250/561, 562, 571, 572, 250/563, 225; 356/237, 431

[56] References Cited

U.S. PATENT DOCUMENTS

| | | | |
|---|---|---|---|
| 2,755,702 | 7/1956 | Cooke . | |
| 3,737,236 | 6/1973 | Borrelli | 250/225 |
| 3,819,948 | 6/1974 | Iijima et al. | 250/225 |
| 4,019,066 | 4/1977 | Lucas et al. . | |
| 4,658,148 | 4/1987 | Naito | 250/571 |
| 4,676,638 | 6/1987 | Yasuda | 356/237 |
| 4,864,123 | 9/1989 | Mizutani et al. | 250/225 |
| 4,931,657 | 6/1990 | Houston et al. | 250/225 |

OTHER PUBLICATIONS

'Optical Measurement Throws New Light on Paper Surface' by Hansuebsai et al., in Pulp Technology and Industry, Aug., 1987, pp. 563-573.
'A Method to Measure Variations in Surface and Diffuse Reflectants of Printed and Unprinted Paper Samples' by Bryntse et al., in Tappi, Apr. 1976, vol. 59, No. 4, pp. 102 to 106.

Primary Examiner—David C. Nelms
Assistant Examiner—K. Shami
Attorney, Agent, or Firm—C. A. Rowley

[57] ABSTRACT

To detect roughness on a travelling surface of a web such as paper a beam of polarized light is directed at an angle onto the web and focused by a focal lens to illuminate a spot on the surface and a specularly reflected component of the light is collected through a second lens focused on the spot. A detector is aligned to receive a portion of the specularly reflected collimated light from the spot passing through a selecting aperture and generates a signal depending on the intensity of the specular light passing through the aperture and received by the detector thereby to provide an indication of the roughness (or smoothness) of the surface.

19 Claims, 3 Drawing Sheets

PAPER ROUGHNESS OR GLASS SENSOR USING POLARIZED LIGHT REFLECTION

FIELD OF THE INVENTION

The present invention relates to a roughness detector collecting specular light reflected from an area on a surface collimating the collected light and passing a portion of the collimated light through an aperture onto a detector to determine the roughness of the surface.

BACKGROUND OF THE PRESENT INVENTION

Many attempts have been made to provide an on-line sensor using reflected light to determine the roughness and in some cases both roughness and gloss of a relatively moving paper sheet, however, to date none have been particularly successful.

One system, described in U.S. Pat. No. 4,019,066 issued Apr. 19, 1977 to Lucas et al, illuminates the web by a light directed at a low angle onto its surface and collects scattered light by a lens system which focuses the collected light as a sharp image through an aperture onto a detector. The detector and associated equipment determine the AC and DC components of the reflected light sensed by the detector and develops a roughness index based primarilty on the ratio of AC to DC signals. This device provides a reasonable correlation between a roughness index and the Sheffield Roughness however the results contain a significant amount of scatter.

U.S. Pat. No. 2,755,702 issued Jul. 24, 1956 Cooke also discloses a system for measuring the smoothness of a surface. In the device microscopic surface characteristics are examined. Light is directed at an oblique angle onto the surface to emphasize irregularities reflected (non-specular) light is viewed through a microscope objective lens and directed through an aperture that serves to restrict the area scanned to dimensions in the order of the microscopic particles. The light passing through the aperture is measured to generate a signal and the signal is analyzed in a spectrum analyzer. The theory of operation is based on the concept that the intensity of deflected light varies in accordance with the shadows formed due to the surface roughness and the oblique lighting.

Projection of a light beam at an angle on the web surface and collection of the specularly reflected component of the light beam has been suggested and applied as described for example in Optical Measurement Throws New Light on Paper Surface by Hansuebsai et al in Pulp Technology and Industry, August 1987, pages 563-573. This paper describes an investigation of the use of different incident angles and an assessment of the use of polarized light, polarized either parallel or perpendicular to determine the best mode of detecting surface properties of paper. Reasonable results were obtained but the sensitivity was lacking.

In a paper entitled 'A Method to Measure Variations in Surface and Diffuse Reflectants of Printed and Unprinted Paper Sample' by Bryntse et al in TAPPI, April, 1976, Volume 59, No. 4, pages 102 to 106, a device similar to that invented by applicant is disclosed. In this device polarized laser light is projected onto a surface and then collected via a lens and projected as an 'image' with a portion of the image passing through a pin hole and focused onto a prism which splits the beam into its perpendicular and parallel polarized components, each of which is independently measured and used to distinguish surface characteristics of the paper sheet. This device, as with the previous devices, has limited sensitivity.

BRIEF DESCRIPTION OF THE PRESENT INVENTION

It is an object of the present invention to provide a sensitive surface roughness detector for on-line detection of the roughness of a commercial grade newsprint sheet paper sheet by sensing light specularly reflected from its surface.

Broadly the present invention relates to an optical sensor comprising means for directing a beam of collimated polarized light from a light source at an angle toward a surface, means for focusing said beam to illuminate an area on said surface having a maximum dimension of less than about 150 microns, means for collecting light from said area including a collimating lens focused on said area and positioned to receive specularly reflected light from said and collimate said reflected light parallel to said specularly reflected light, an aperture aligned to pass a portion of said collimated specularly reflected light from said area, a lens for focusing said portion of said collimated specularly reflected light passing through said aperture onto a detector, said detector detecting the instantaneous intensities of said specularly reflected light passing through said aperture to generate a signal representative of the instantaneous intensities of said specularly reflected light received by said detector to provide an indication of variation in intensities of said specularly reflected light and thereby an indication of surface properties of said surface.

Preferably said polarized light will be perpendicularly polarized in a plane perpendicular to said surface and preferably said detector will detect substantially only the perpendicularly polarized portion of the specularly reflected light.

Preferably said angle will be between about 45° and 80° from a perpendicular to said surface and more preferably said angle will be Brewster's angle.

Preferably said light source will comprise a laser.

Preferably said light source and said detector will be on substantially parallel axes, and mirror means positioned to direct light from said means for focusing on said area and to focus said collimating lens on said area.

BRIEF DESCRIPTION OF THE DRAWINGS

Further features, objects and advantages will be evident from the following detailed description of the preferred embodiments of the present invention taken in conjunction with the accompanying drawings in which.

DESCRIPTION OF THE PREFERRED EMBODIMENTS

Figure 1:
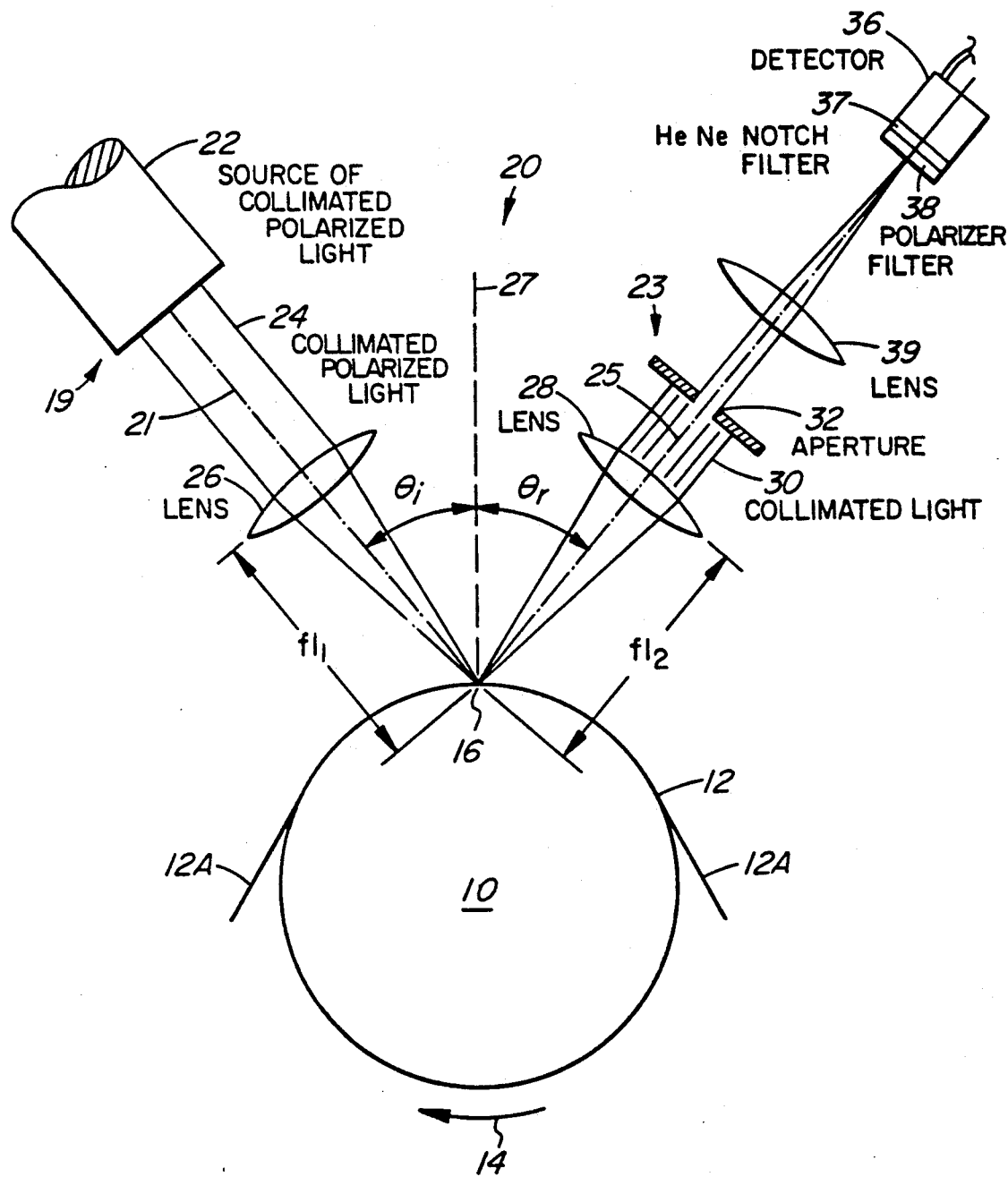
FIG. 1 is a schematic illustration of a model of a device incorporating the present invention.

In the layout shown in FIG. 1 which illustrates an in-the-lab adaption of the present invention, which includes a rotating cylinder 10 on which a sample to be examined is mounted, the cylinder 10 rotates as indicated by the arrow 14 and advances axially so that different points or areas 16 are illuminated as the sample 12 is rotated and advanced by the drum 10.

It will be apparent that in an on-line arrangement of the present invention a web of paper would simply pass over and be supported by a rotary drum 10 which holds the web in proper position relative to the sensor 20. Such a web is schematically indicated at 12A in FIG. 1.

The sensor 20 of the present invention includes a light emitting and directing system 19 which comprises a source of collimated polarized light 22 and directs the collimated polarized light as indicated at 24 onto a focusing lens 26 focused onto the spot or area 16 illuminated by the light. The light is focused onto the spot 16 at angle $\Theta_i$ measured from the perpendicular 27 to the surface of spot 16 to the focal axis 21 of the laser or other source of light 22. The spot or area 16 has a major dimension that normally would not exceed 150 microns. The size (area) of the illuminated area or sport 16 will be sufficiently small that the specular reflection from the spot 16 is significantly modified due to inherent roughness of the surface of the web 12 as opposed to gloss or general reflectance of the surface although with the present invention it has been found that the specularly reflected light is indicative (but with different sensitivity) of both roughness and gloss.

The focal length $fl_1$ of the lens 26 defines the distance between the lens 26 and the spot 16.

On the detector side or receiving side of the instrument or sensor 20 there is provided a detector system 23 having a focal axis 25. A detecting lens 28 which is focused onto the spot 16 and collimates the light collected from the spot 16 as indicated at 30 substantially parallel to the specularly reflected light so that only specularly reflected light or substantially specularly reflected light is passed through an aperture 32 which is aligned with the specular angle. The specularly reflected light passing through the aperture 32 is focused by a lens 34 onto a detector 36 that preferably is provided with a HeNe notch filter 37 (i.e. to tend to limit the light to that generated by the light source 22) and with polarizer filter 38 permitting passage of light polarized in the same direction as the collimated polarized light 24 directed onto the spot 16.

The angle $\Theta_r$ measured between the perpendicular 27 to the surface 12 and the focal axis 25 of the detector system 23 will be equal to the angle $\Theta_i$, i.e. will be specular angle and the focal length $fl_2$ of the lens 28 will define the position of the lens 28 relative to the spot 16 and will preferably be substantially equal to or greater than the focal length $fl_1$ of the lens 26.

The focal length $fl_1$ will be in the range of 30 to 200 mm, preferably 75 to 150 mm. The angle $\Theta_i$ and $\Theta_r$ as above indicated will be substantially equal so that the lens 28 collects specularly reflected light from the spot 16 and eh angle $\Theta_i$ will preferably be greater than about 45° and less than 80°. Preferably $\Theta_1$ and $\Theta_2$ will be set at Brewster's angle namely 57° for paper.

The collimated polarized light 24 will preferably be polarized substantially perpendicularly, i.e. perpendicular to the surface of the sample 12 or 12A and the polarizer filter 38 will only permit the passage of like polarized light.

It will be apparent from the above description that the light received by the detector 36 is substantially solely restricted to specularly reflected light emanating from the source 22 and is further limited by the filter 38 so that the sensitivity of the system is maximized.

Figure 2:
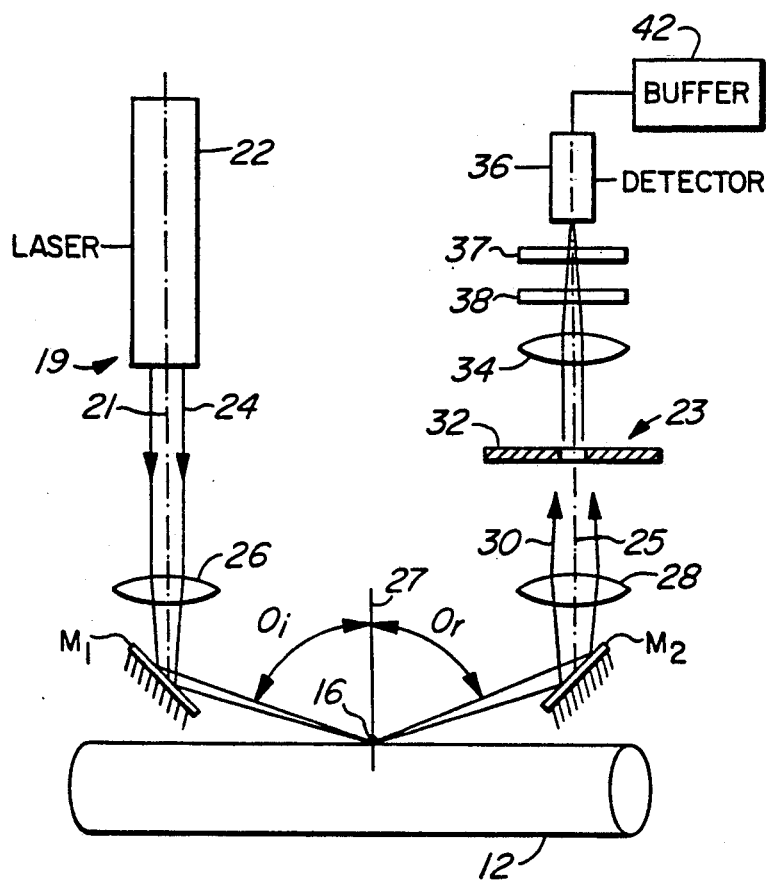
FIG. 2 is a schematic illustration of a second version of the device incorporating mirrors to permit more convenient monitoring of the light source and detector systems.

The arrangement shown in FIG. 2 is essentially the same as that shown in FIG. 1, however the light from the lens 26 is reflected via the mirror $M_1$ to bend the extension focal axis 23 from the line 26 to intersect the surface 12 at spot 16 at the requisite angle $\Theta_i$ and the lens 28 is focused off of mirror $M_2$ which hands the extension of the focal axis 25 from the line 28 onto the spot 16 at the angle $\Theta_2$. This permits the laser 22 (source of collimated polarized light) and the detector 36 to be positioned with this focal axis 23 and 25 to receive light along substantially parallel axes (or any other selected axis) in relatively close proximity to each other to make the unit more compact and/or facilitate mounting on the machine.

Figure 3:
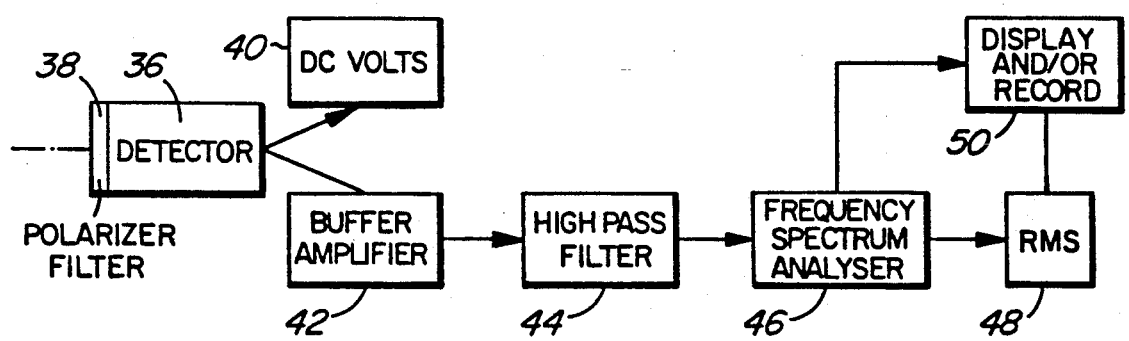
FIG. 3 is a schematic illustration of the detector of the present invention.

Referring to FIG. 3, the light passing through the polarizer filter 38 and received by the detector 36 generates a signal in the detector 36 that contains an AC signal and a DC signal. DC voltage signal is measured as indicated at 40 and the AC signal is passed to a buffer amplifier 42, a high pass filter 44 and specturm analyzer 46 or, for example, a true AC RMS voltmeter such as the Phillips PM 2525 interfaced to a computer via an RS232 line may be used. The root means square of the AC signal is determined as indicated at 48 and used to define roughness (or gloss) of the surface 12. The root means square may be displayed in a desired form as indicated at 50.

Figure 4:
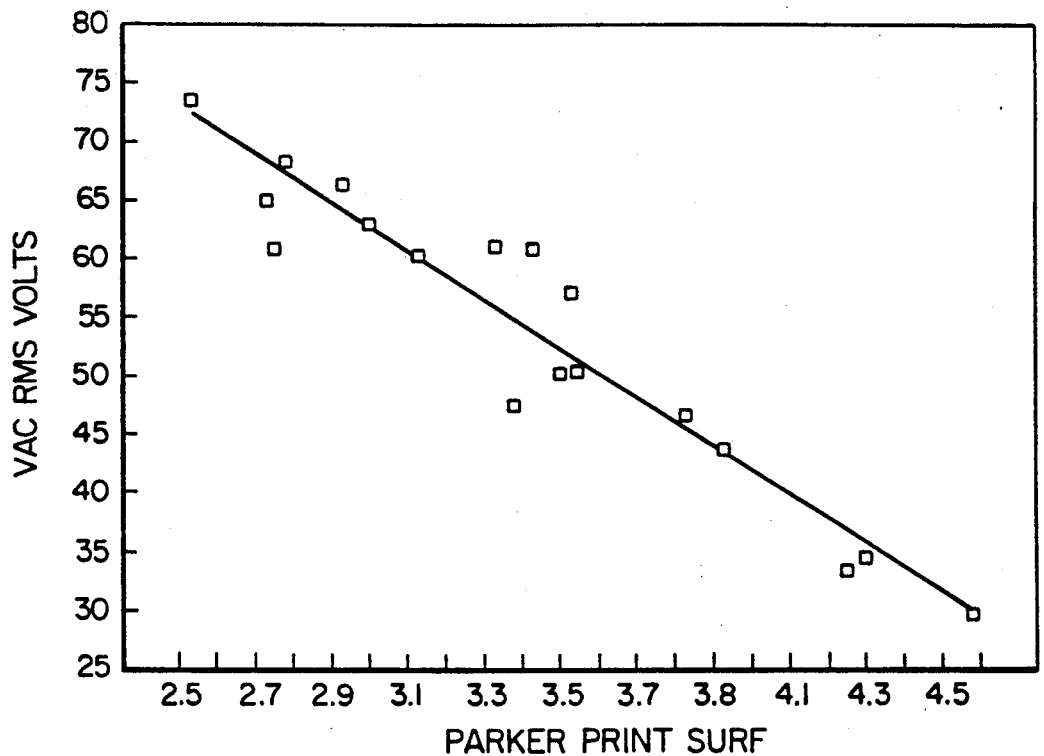
FIG. 4 is a plot of the root mean square of the AC voltage in millivolts vs the Parker Print Surface reading for the same paper.

FIG. 4 shows a plot of readings obtained using the present invention in AC RMS mV (millivolts) vs Parker Print Surf (microns) and shows a very clear and significant change in millivolt readings correlating well with different Parker Print Surf readings in the range, particularly of 2.8 to 3.4 μm which is an important region in the analysis of newsprint. The results plotted in FIG. 4 were obtained using a focusing lens 26 having a focal length of $fl_1$ 30 mm and a diameter of 17 mm directing light from a laser having a power of 2 mw projecting light of a wave length of 0.63 μm and linearly polarized parallel to a plane perpendicular to the surface 12. Both the collecting lenses 28 and 34 had focal lengths of $fl_2$ 100 mm and diameters of 50 mm. The optical filter had a centre wave length of 0.633 μm, a band width of 0.01 μm and a peak transmission of 66% while the photo diode of the detector 36 had an area of 0.8 mm$^2$. The angles $\Theta_i$ and $\Theta_r$ were both equal to 56°. The area 16 had a diameter of 100 microns and the aperture 32 was 3.5 mm in diameter.

Figure 5:
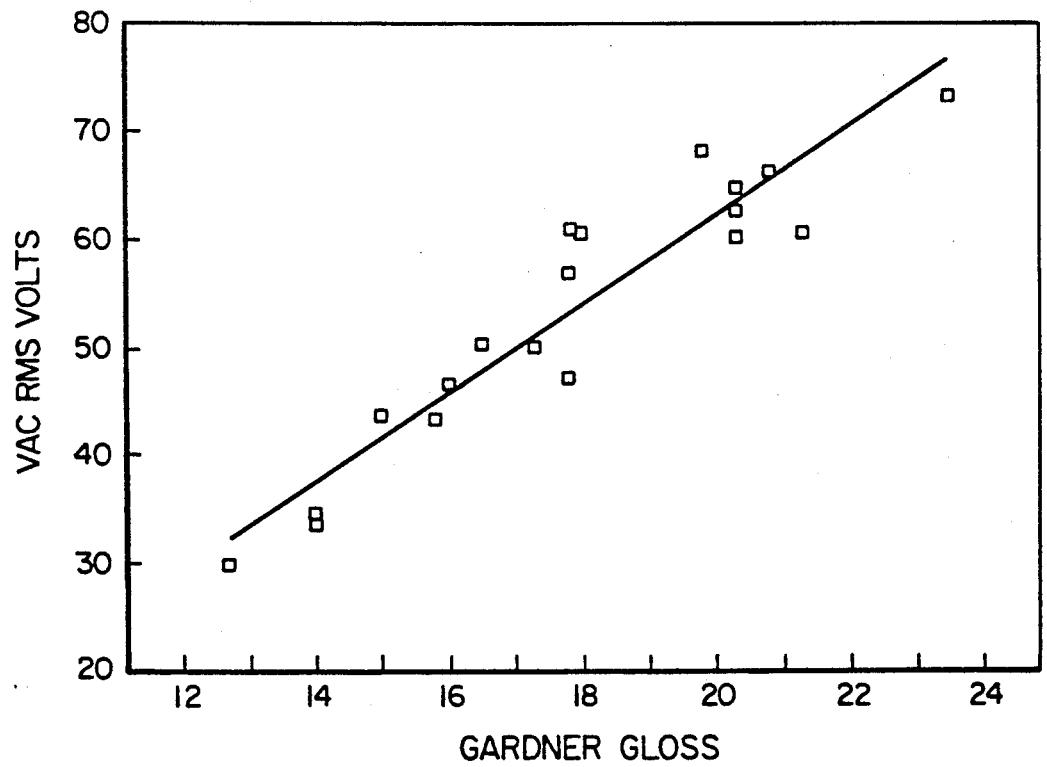
FIG. 5 is a graph similar to FIG. 3 but wherein the volts AC are plotted against Gardner Gloss readings for the same paper.

FIG. 5 shows a correlation between the optical roughness in volts AC RMS millivolts obtained using the same equipment as the results plotted in FIG. 4 versus the Gardner Gloss reading. A very good correlation is shown between Gardner Gloss and millivolts thereby illustrating the significant sensitivity of the present invention to Gardiner Gloss but on a different scale.

It will be apparent from FIGS. 4 and 5 that the instrument generates a significantly wide range of signal that correlates well with both GArdner Gloss and more imporant with Parker Print Surf in the desired range and therefore provides a good on-line system for measuring printability as depicted for example by the Parker Print Surf reading normally used for this purpose.

Having described the invention, modifications will be evident to those skilled in the art without departing from the spirit of the invention as defined in the appended claims.

I claim:

1. An optical sensor for determining the roughness or gloss of a paper web comprising means for directing a beam of collimated polarized light from a light source at an angle toward a surface of said paper web travelling relative to said light source, means for focusing said beam on said suface to illuminate a spot on said surface, said spot having maximum dimension of less than one hundred and fifty microns, collecting light reflected from said spot illuminated on said surface through a collimating lens focused at said spot illuminated on said surface and positioned to receive specularly reflect light from said light source reflected from said spot illuminated on said surface and collimate said reflected light parallel to said specularly reflected light, an aperture aligned to pass a portion of said collimated specularly reflected light from said spot, a lens for focusing said portion of said collimated specularly reflected light passing through said aperture onto a detector, said detector detecting the instantaneous intensities of said specularly reflected light passing through said aperture to generate a signal representative of the instantaneous intensities of said specularly reflected light received by said detector, a high pass filter through which said generated signal is passed to provide an AC signal, means for determining the root means square of said AC signal to provide an indication of surface roughness or gloss of said surface.

2. A sensor as defined in claim 1 wherein said means to polarize polarizes light perpendicularly in a plane perpendicular to said surface and wherein said detector includes means for transmitting substantially only the perpendicularly polarized portion of the specularly reflected light.

3. A sensor as defined in claim 1 wherein said angle is between about 50° and 75° from a perpendicular to said surface.

4. A sensor as defined in claim 2 wherein said angle is between about 50° and 75° from a perpendicular to said surface.

5. A sensor as defined in claim 2 wherein said angle is Brewster's angle for material being sensed.

6. A sensor as defined in claim 1 wherein said light source comprises a laser.

7. A sensor as defined in claim 2 wherein said light source comprises a laser.

8. A sensor as defined in claim 3 wherein said light source comprises a laser.

9. A sensor as defined in claim 4 wherein said light source comprises a laser.

10. A sensor as defined in claim 5 wherein said light source comprises a laser.

11. A sensor as defined in claim 1 wherein said light source and said detector have their focal axes substantially parallel, a first mirror means positioned to direct light from said means for focusing onto said surface at said angle and second mirror means positioned to focus said collimating lens onto said surface.

12. A sensor as defined in claim 2 wherein said light source and said detector have their focal axes substantially parallel, a first mirror means positioned to direct light from said means for focusing onto said surface at said angle and second mirror means positioned to focus said collimating lens onto said surface.

13. A sensor as defined in claim 3 wherein said light source and said detector have their focal axes substantially parallel and a first mirror means positioned to direct light from said means for focusing onto said spot at said angle and second mirror means positioned to focus said collimating lens onto said spot.

14. A sensor as defined in claim 4 wherein said light source and said detector have their focal axes substantially parallel and a first mirror means positioned to direct light from said means for focusing onto said spot at said angle and second mirror means positioned to focus said collimating lens onto said spot.

15. A sensor as defined in claim 5 wherein said light source and said detector have their focal axes substantially parallel and a first mirror means positioned to direct light from said means for focusing onto said spot at said angle and second mirror means positioned to focus said collimating lens onto said spot.

16. A sensor as defined in claim 6 wherein said light source and said detector have their focal axes substantially parallel and a first mirror means positioned to direct light from said means for focusing onto said spot at said angle and second mirror means positioned to focus said collimating lens onto said spot.

17. A sensor as defined in claim 7 wherein said light source and said detector have their focal axes substantially parallel and a first mirror means positioned to direct light from said means for focusing onto said spot at said angle and second mirror means positioned to focus said collimating lens onto said spot.

18. A sensor as defined in claim 8 wherein said light source and said detector have their focal axes substantially parallel and a first mirror means positioned to direct light from said means for focusing onto said spot at said angle and second mirror means positioned to focus said collimating lens onto said spot.

19. A sensor as defined in claim 10 wherein said light source and said detector have their focal axes substantially parallel and a first mirror means positioned to direct light from said means for focusing onto said spot at said angle and second mirror means positioned to focus said collimating lens onto said spot.

* * * * *

UNITED STATES PATENT AND TRADEMARK OFFICE
CERTIFICATE OF CORRECTION

PATENT NO. : 5,162,660
DATED : November 10, 1992
INVENTOR(S) : Roman E. Popil

It is certified that error appears in the above-indentified patent and that said Letters Patent is hereby corrected as shown below:

On the title page, item [54] and in column 1, line 2, in the title change "Glass" to "Gloss".

Signed and Sealed this

First Day of February, 1994

Attest:

BRUCE LEHMAN

*Attesting Officer*  *Commissioner of Patents and Trademarks*